US012611244B1

(12) United States Patent
Kreindel

(10) Patent No.: US 12,611,244 B1
(45) Date of Patent: Apr. 28, 2026

(54) DEVICE AND METHOD FOR TREATMENT OF NASAL SEPTUM

(71) Applicant: INMODE LTD., Yokneam (IL)

(72) Inventor: Michael Kreindel, Richmond Hill (CA)

(73) Assignee: INMODE LTD., Yokneam (IL)

( * ) Notice: Subject to any disclaimer, the term of this patent is extended or adjusted under 35 U.S.C. 154(b) by 980 days.

(21) Appl. No.: 17/517,790

(22) Filed: Nov. 3, 2021

(51) Int. Cl.
  *A61B 18/14* (2006.01)
  *A61B 18/00* (2006.01)
(52) U.S. Cl.
  CPC .... *A61B 18/14* (2013.01); *A61B 2018/00077* (2013.01); *A61B 2018/00083* (2013.01); *A61B 2018/00327* (2013.01); *A61B 2018/00577* (2013.01); *A61B 2018/143* (2013.01)
(58) Field of Classification Search
  CPC .......... A61B 18/14; A61B 2018/00077; A61B 2018/00083; A61B 2018/00327; A61B 2018/00577; A61B 2018/143
  See application file for complete search history.

(56) References Cited

U.S. PATENT DOCUMENTS

| | | | | |
|---|---|---|---|---|
| 6,109,268 | A | * | 8/2000 | Thapliyal ........... A61B 18/1485 606/41 |
| 11,896,293 | B2 | * | 2/2024 | Kreindel ............ A61B 18/1485 |
| 2012/0323232 | A1 | * | 12/2012 | Wolf ........................ A61N 1/40 606/1 |
| 2014/0200581 | A1 | * | 7/2014 | Aluru ................... A61B 18/042 606/41 |
| 2022/0015824 | A1 | * | 1/2022 | Horie ................. A61B 18/1485 |

* cited by examiner

*Primary Examiner* — Joseph A Stoklosa
*Assistant Examiner* — Annie L Shoulders
(74) *Attorney, Agent, or Firm* — ALLEN, DYER, DOPPELT + GILCHRIST, P.A.

(57) ABSTRACT

The nasal septum is reshaped by creating multiple holes in the cartilage. RF energy can be applied to ablate tissue around the holes in a manner that minimizes damage of surrounding epithelial and mucosal tissues.

20 Claims, 7 Drawing Sheets

11

12

13

11

12

DEVICE AND METHOD FOR TREATMENT OF NASAL SEPTUM

FIELD OF THE INVENTION

The invention relates to reshaping cartilage tissue through the formation of multiple perforations, and more particularly, to a device and method for treatment of the nasal septum thereby.

BACKGROUND OF THE INVENTION

Septoplasty surgery is the main method for fixing a deviated septum. The surgery requires general anesthesia and the associated long recovery time. An alternative method of cartilage reshaping is described in U.S. Pat. No. 6,589,235, which discloses holding and deforming cartilage to a desired final shape and imparting radiofrequency (RF) energy in order to raise the cartilage temperature to achieve stress relaxation occurs. After stress relaxation, the cartilage maintains a new shape. The cartilage should be heated up to 60-75° C., and the method also includes tissue temperature monitoring and RF energy control according to temperature measurements. Nasal septum cartilage reshaping was identified as one of the applications for the above mentioned treatment method.

A similar method is described in U.S. Pat. No. 9,125,677, which describes using laser energy delivered through an optical fiber is used to elevate cartilage temperature and reduce mechanical stress from shaped cartilage.

The family of patents including U.S. Pat. Nos. 11,033,318, 10,932,853, 10,779,873, 10,722,282, 10,631,925, 10,485,603, 10,456,186, 10,456,185, 10,398,489, 10,376,300, 10,335,221, 10,265,115, 10,028,780, 9,913,682, 9,788,886, 9,687,296, 9,526,571, 9,486,278, 9,452,010, 9,433,463, 9,237,924, 9,179,967, 9,179,964, 9,072,597, and 8,986,301 use similar methods for cartilage reshaping and describe different designs and methods for nasal valve collapse and nasal septum treatment. The methods include applying energy to the cartilage directly through the incision in the soft tissue or non-invasively through the mucosal layer. Different shapes of electrodes are discussed and monitoring of the tissue temperature is described. A limitation of the method is the large burn in mucosal tissue resulting from heating of cartilage up to 60° C. and above. This burn may result in pain, dryness and bleeding.

U.S. Pat. No. 10,603,059 describes method for nasal septum treatment where a substance modifying the property of cartilage is injected and then RF energy and deformation force are applied to deactivate the injected substance.

The method of fractional ablation is used in aesthetic medicine for skin remodeling and includes laser ablation of the skin with laser (U.S. Pat. No. 7,295,358) with RF energy (U.S. Pat. No. 8,771,268) and mechanical perforation (U.S. Pat. No. 10,716,591). A similar method can be used for cartilage reshaping with the procedure adjusted for the new tissue type and specific medical needs.

SUMMARY OF THE INVENTION

In view of the foregoing, the present invention provides a device and method for reshaping the nasal tissue by creating multiple holes in the cartilage. The device comprises a hand piece having a handle on a proximal end and a disposable tip on a distal end. The disposable tip has one or more elements to create holes in the cartilage tissue. The diameter of the holes should be not more than 2 mm to keep cartilage tissue intact, while the number and density of the holes should be enough to reduce mechanical stress and reshape the cartilage tissue.

The holes in the cartilage can be created mechanically using sharp needles or rotating cylindrical elements. Alternatively, the holes can be created by thermal ablation of the tissue using electrical or optical energy. Radiofrequency (RF) energy, ultrasound or laser radiation can be used to create tissue ablation. The power density should be high enough to create evaporation of the treated tissue without significant lateral heat. Especially, it is important to minimize thermal damage of epithelial layer which has important function in filtering air and hydrating the nasal cavity.

The holes in the cartilage can be created through the entire thickness of thereof across the nasal septum or to the limited depth which is enough to remove mechanical stress in the cartilage. The total density of holes should not exceed 30% of total treated area.

The smaller holes, the faster the healing process will be. The practical range of hole diameter is from 0.1 millimeter (mm) up to 2 mm. The shape of hole can be cylindrical, conical, rectangular, pyramidal or any other shape, and is generally determined by the needle shape.

A combination of mechanical perforation and energy ablation can be used. The combination has advantage when the elements penetrate the epithelial layer mechanically and ablate larger hole in cartilage. This method allows an optimized healing process and preserves the epithelial surface from the thermal damage.

In one embodiments, a matrix of needles is used where a base part of the needles is coated with electrically insulative material while the end part of the needles is conductive and delivers RF energy to ablate the cartilage and create the larger hole. The RF power should be comparable with typical electrosurgical devices operated in cutting mode and be in the range of 10 watts (W) up to 400 W total for the matrix.

Alternatively, holes can be created by laser ablation where laser radiation is delivered through the optical fiber or hand piece focusing radiation in a small spot. A scanner can be used to create multiple holes in a predetermined area. Usually, infrared radiation is used for tissue ablation including diode lasers, Nd: YAG, Er: YAG, CO2 lasers and other lasers generating optical radiation in the range of 700 nanometers (nm) to 12 micrometers (μm).

For mechanical perforation, a plate applied to the opposite side of the tissue can be used to provide counter force during mechanical perforation of the tissue. The hand piece can also be designed as a plyer where needles are located on one or both sides of the elements contacting the tissue. The plate applied to the opposite side of the tissue can be used as return electrode or second bi-polar electrode when RF energy is used to assist the tissue ablation.

Special clips or tampons can be used to deform the tissue during the healing process to preserve a new shape of the treated cartilage. This method can be used for reshaping any cartilage including nasal valve, nasal septum, ears and other anatomical areas comprising cartilage and requiring reshaping for medical or aesthetic conditions.

3

Figure 1:
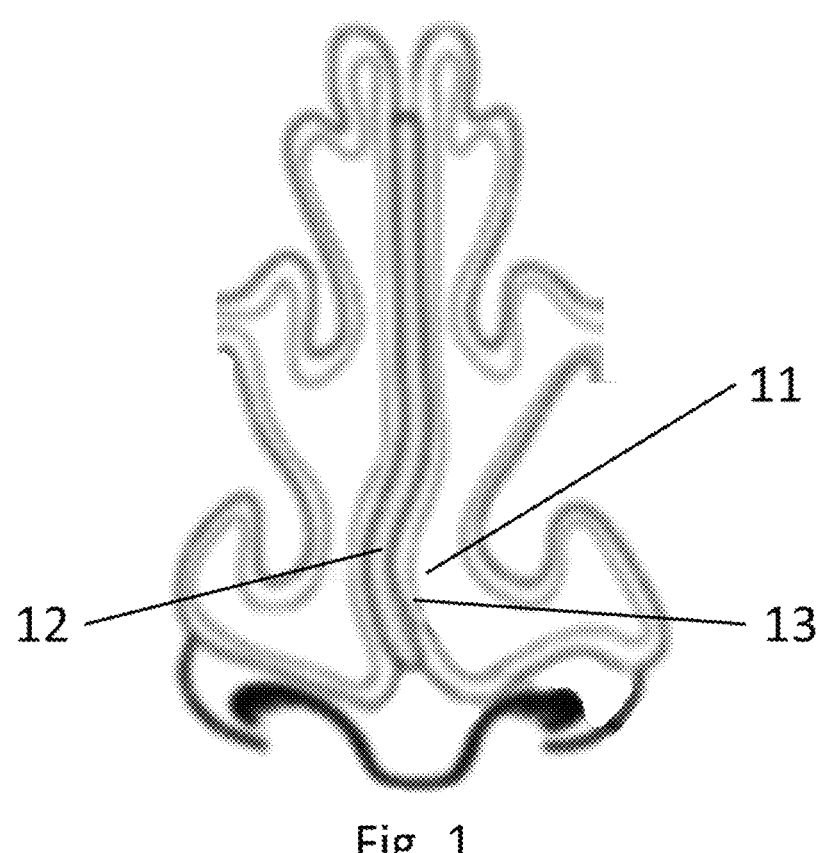
FIG. 1 is a cross-section of a nose with a deviated nasal septum.
Figure 2:
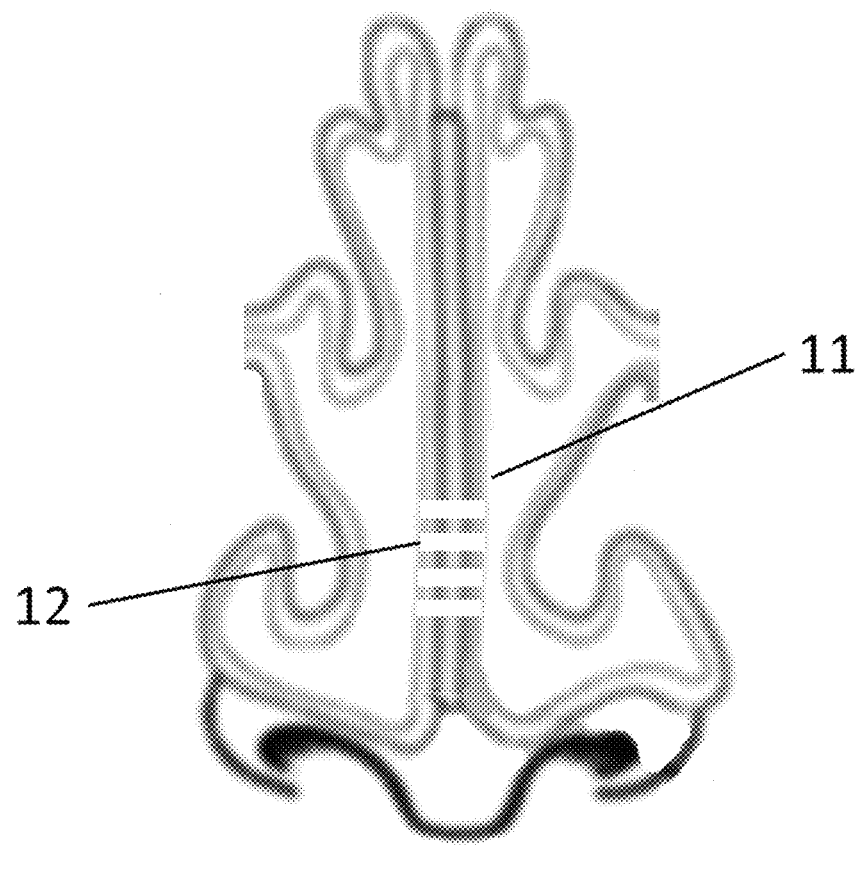
Figure 3:
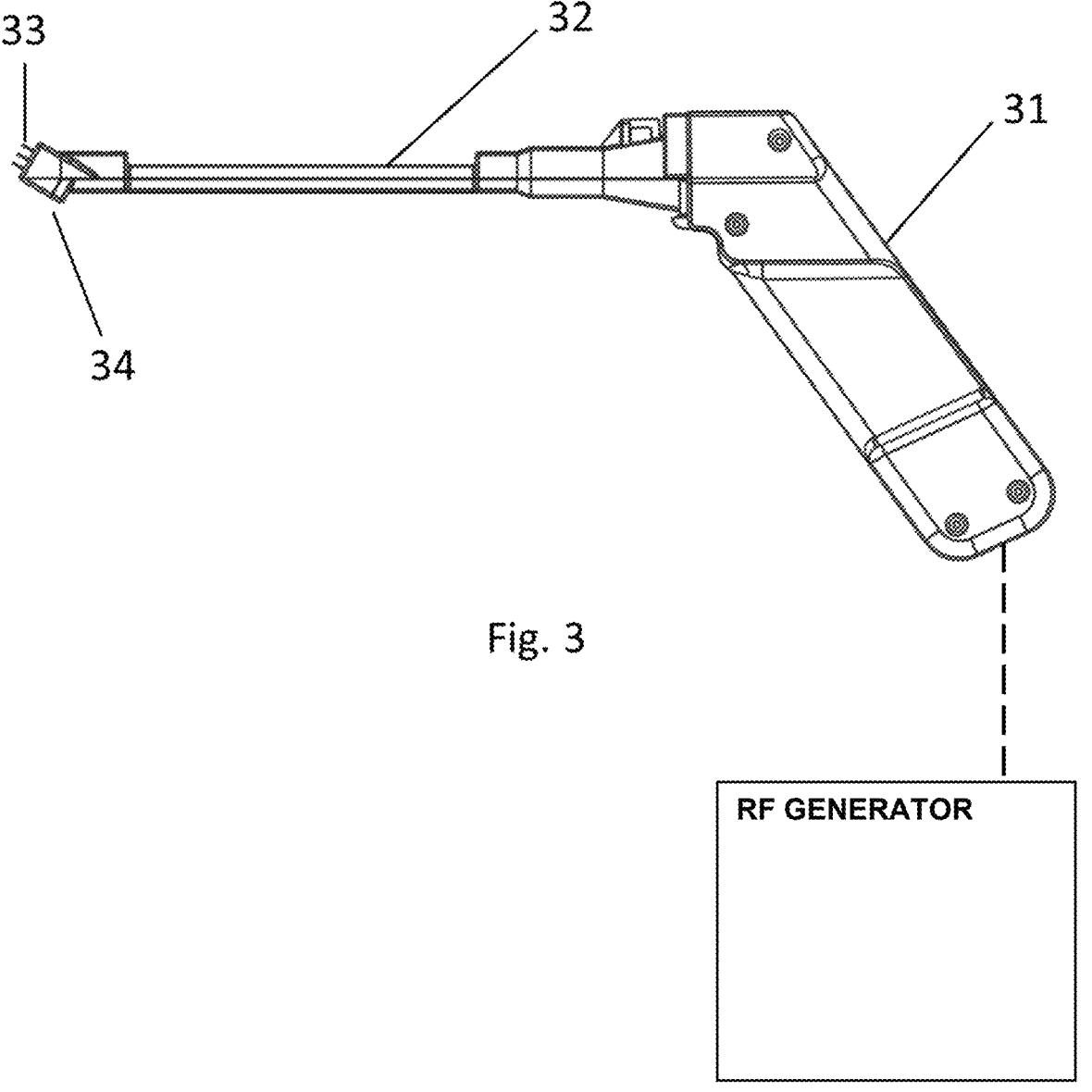
Figure 4:
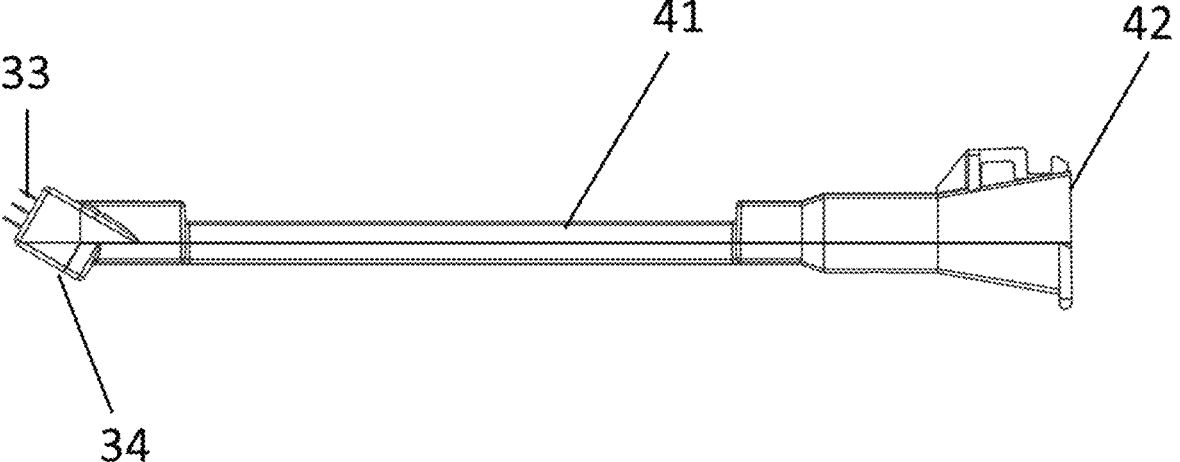
Figure 5:
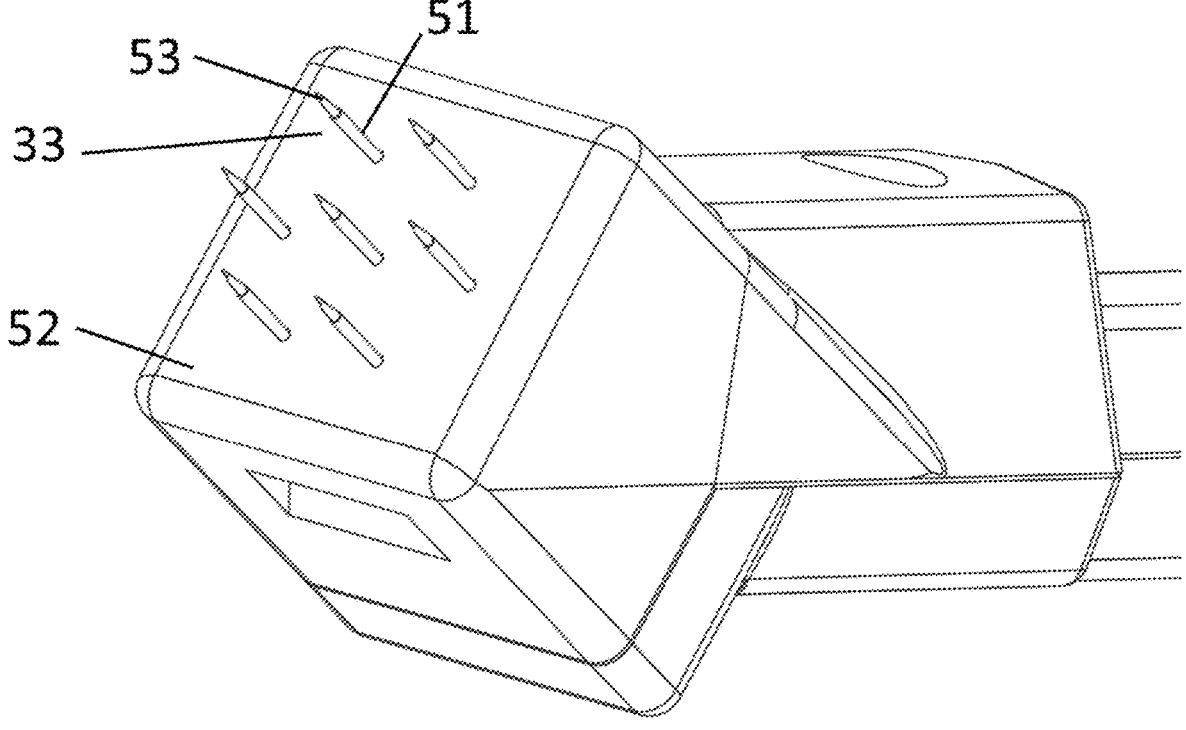
Figure 6:
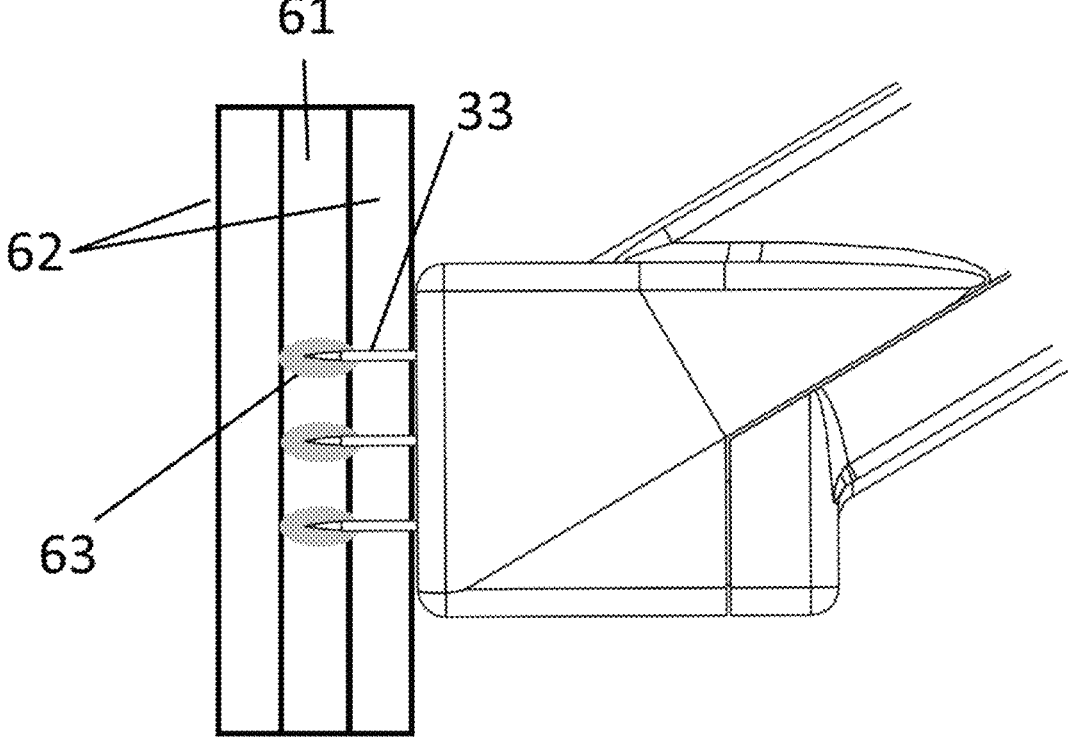
Figure 7:
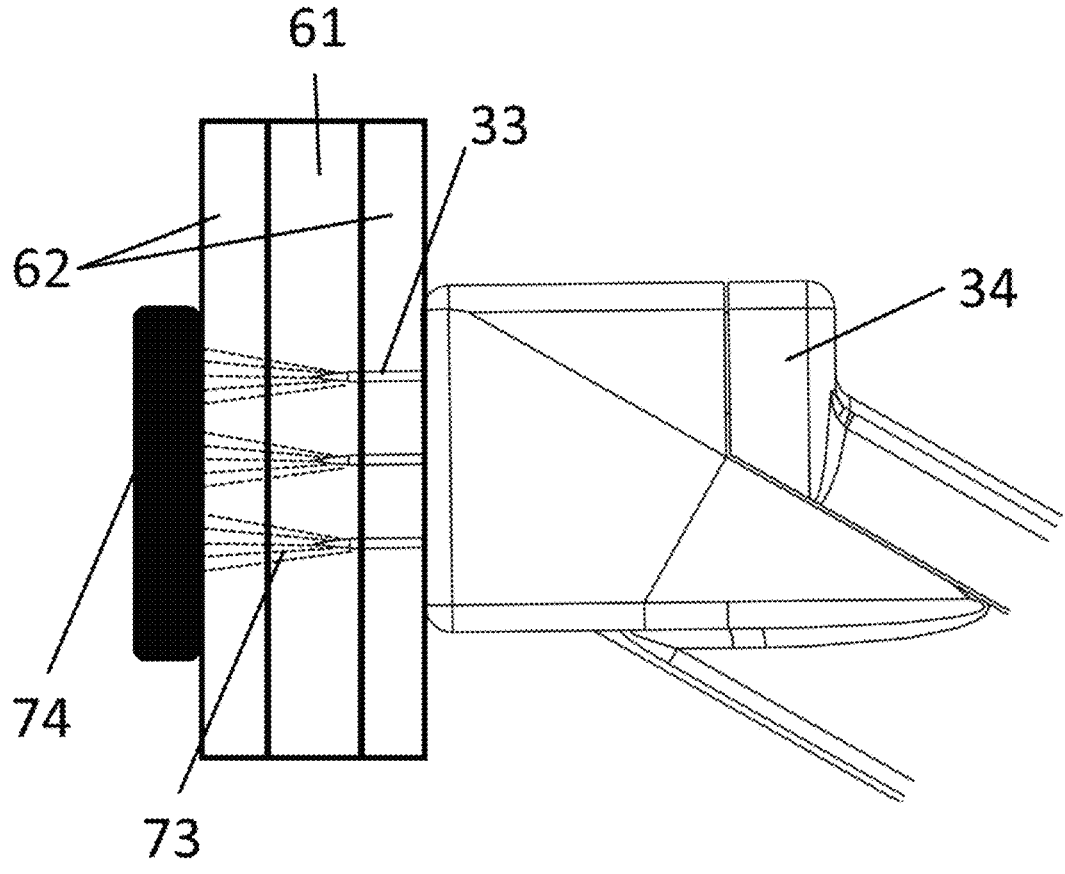

FIG. 2 is a cross-section of the nose of FIG. 1 after forming multiple holes in the nasal septum and flattening the nasal septum;

FIG. 3 is a side view of a device for treatment of the nasal septum according to an embodiment of the present invention, having a handpiece with a disposable tip;

FIG. 4 is a side view of the disposable tip of FIG. 3;

FIG. 5 is a perspective view of distal end of the disposable tip of FIG. 3, including a plurality of conductive needles;

FIG. 6 is a schematic presentation of the distal end of the disposable tip of FIG. 3 applied to a portion of nasal septum being treated; and FIG. 7 is a schematic presentation of the distal end of the disposable tip of FIG. 3 applied to a portion of nasal septum being treated, according to an alternate embodiment utilizing a return electrode applied to an opposite side of the nasal septum.

DETAILED DESCRIPTION OF PREFERRED EMBODIMENTS

Referring first to FIG. 1, a cross-section of the nose with a deviated nasal septum 11 is shown. The nasal septum 11 comprises a cartilage layer 12 and mucosal layers 13 covering the cartilage layer 12. The deviated cartilage 12 of deviated nasal septum 11 blocks the nasal airway, impeding normal breathing. The excessive amount of cartilage 12 and mechanical elasticity of the cartilage would typically require surgical intervention to fix the problem.

In FIG. 2, multiple holes have been formed in the nasal septum to remove excessive cartilage and reduce mechanical stress, allowing the cartilage 12 to be flattened. This minimal intervention allows fast healing of the nasal septum 11 in its new, more flattened, shape. Proper healing after the procedure is achieved by inserting tampons into the nostrils, ensuring proper positioning of the treated nasal septum during the healing. It is important during the treatment to minimize damage to mucosal layer 13.

Referring to FIG. 3, a hand piece with disposable tip 32 is shown. The hand piece is connected to a radiofrequency (RF) generator. The hand piece comprises a handle 31 and the disposable tip 32 attached to the handle 31. At the distal end 34 of the disposable tip 32 there are needle electrodes 33. RF energy from the RF generator is delivered to the treated tissue through the needle electrodes 33. RF power delivered to tissue through the needle electrodes 33 is high enough to create ablation and coagulation of tissue in vicinity of the needle electrodes 33.

Referring to FIG. 4, the disposable tip 32 has proximal end with connector 42 for releasable connection to the handle 31. The shaft 41 connects the proximal end 42 with the distal end 34, which carries the needle electrodes 33. The distal end 34 of is inserted into the nose and engages the area to be treated via the electrodes 33. RF energy is delivered to the needle electrodes 33 preferably in the range of 10 millijoules (mJ) to 10 joules (J) per needle. Energy can be delivered in a continuous pulse or a train of pulses, with RF energy delivery time in the range of 1 millisecond (ms) to tens of second. Delivered RF energy should be high enough to cause tissue ablation around the needle electrodes 33.

Referring to FIG. 5, a base 51 of each needle electrode 33 contacting is made from a dielectric material and multiple needle electrodes 33 are arranged over the skin contacting surface 52 of the distal end 34. The needle electrodes 33 each have a sharp conductive end 53 extending from the insulated part 51 coated with dielectric material. This structure of the needle electrodes 33 allows ablation of cartilage without thermal damage of epithelial and mucosal tissues.

Referring to FIG. 6, the distal end 34 of disposable tip 32 is applied to tissue to be treated. The needle electrodes 33 penetrate into the tissue and RF energy is applied through the conductive needle end 53 into the cartilage layer 61 while insulated base 51 of the needle is in contact with more superficial mucosal layer 62. When the user applies pressure with the hand piece to the treated tissue and the needle electrodes 33 penetrate mechanically into the cartilage tissue 61, creating holes through part or the entire tissue 61 thickness. RF energy applied to the needles ablates cartilage around the needle increasing the diameter of the hole 63 in the cartilage layer 61 without increasing damage in the mucosal tissue 62.

In the FIG. 6, RF energy is applied between the needle electrodes 33. Referring to FIG. 7, in an alternate embodiment, RF current is applied between the needle 33 and a return electrode 74 applied to the opposite side of the tissue. Directional RF current flow 73 from the needle 33 to the return electrode 74 ablate the cartilage 61 while thermal effect in the mucosal layer 62 near the return electrode 74 has less heating due to the divergence of RF current 73.

The preferred parameters for the treatment method are:
1. Typical hole diameter is in the range of 0.1 mm to 1.5 mm
2. Hole depth should be at least through the 30% of cartilage thickness to reduce mechanical stress of cartilage tissue
3. Density of holes in cartilage is from 2% up to 30% of the treated area.

The preferred parameters of the device are
1. Diameter of needles is 0.1 mm to 1 mm
4. Average RF power per needle is in the range of 1 W to 100 W which can be delivered in pulsed, CW or quasi-CW mode
5. Frequency of RF is from 0.2 MHz up to 10 MHz

What is claimed is:

1. A method for treatment of a deviated nasal septum of a nose, the method comprising:

forming a plurality of holes in only cartilage of the nasal septum using a plurality of needle electrodes arranged in a matrix and inserted through a superficial mucosal layer to remove excess tissue and reduce mechanical resistance;

applying pressure to flatten the nasal septum with the plurality of holes formed therein; and maintaining the flattened nasal septum while healing to achieve a new shape allowing better air flow through the nose;

wherein each of the needle electrodes arranged in the matrix includes a conductive end extending beyond an insulated section.

2. The method of claim 1, wherein forming the plurality of holes includes penetrating portions of the cartilage with a mechanical instrument.

3. The method of claim 1, wherein forming the plurality of holes includes thermally ablating portions of the cartilage.

4. The method of claim 3, wherein the thermally ablating the portions of the cartilage includes applying radiofrequency (RF) energy to the portions of the cartilage to achieve the thermal ablation.

5. The method of claim 4, wherein applying RF energy to the portions of the cartilage includes inserting the plurality of needle electrodes arranged in the matrix into the cartilage from one side of the nasal septum.

6. The method of claim 1, wherein at least a portion of the plurality of holes are formed to extend through an entire thickness of the cartilage.

7. The method of claim 1, wherein at least a portion of the plurality of holes are formed to extend only partially through an entire thickness of the cartilage.

8. The method of claim 7, wherein at least a portion of the plurality of holes are formed to extend through at least 30% of the entire thickness of the cartilage.

9. The method of claim 1, wherein each of the plurality of holes are formed with a diameter of 0.1 millimeters (mm) to 1.5 mm.

10. The method of claim 1, wherein a collective area of the plurality of holes is between 2% and 50% of a total area of the nasal septum being treated.

11. A method for treatment of a deviated nasal septum of a nose, the method comprising:

inserting a distal end of a tip of handpiece into the nose;

penetrating cartilage of the nasal septum with a plurality of needle electrodes arranged in a matrix extending from the distal end;

applying radiofrequency (RF) energy with the plurality of needle electrodes arranged in the matrix and inserted through a superficial mucosal layer to ablate portions of only the cartilage adjacent thereto; and reshaping the nasal septum after ablating the portions of the cartilage;

wherein each of the needle electrodes arranged in the matrix includes a conductive end extending beyond an insulated section.

12. The method of claim 11, wherein penetrating the cartilage of the nasal septum includes extending the conductive ends of the plurality of needle electrodes arranged in the matrix into the cartilage with the insulated sections extending through overlying epithelial and mucosal tissues.

13. The method of claim 12, wherein the RF energy is applied from only the conductive ends of the plurality of needles.

14. The method of claim 11, wherein applying the RF energy is applied at a power level sufficient to vaporize the portions of the cartilage.

15. The method of claim 14, wherein holes are formed through an entire thickness of the cartilage due to the vaporization.

16. The method of claim 11, wherein the RF energy is applied between the plurality of needle electrodes.

17. The method of claim 11, wherein the RF energy is applied from the plurality of needle electrodes and at least external electrode applied to an opposite side of the nasal septum.

18. The method of claim 11, wherein a diameter of each of the plurality of needle electrodes is between 0.1 millimeters (mm) and 1.0 mm.

19. The method of claim 11, wherein an average power of the RF energy applied by each of the plurality of needle electrodes is between 1 watt (W) to 100 W.

20. The method of claim 11, wherein a frequency of the RF energy applied by the plurality of needle electrodes is between 0.2 megahertz (MHz) and 10 MHz.

* * * * *